United States Patent
Liou

(10) Patent No.: US 11,351,400 B2
(45) Date of Patent: Jun. 7, 2022

(54) BIOLOGICAL OBJECT IMAGE-CAPTURING AND TREATMENT SYSTEM AND METHOD

(71) Applicant: Taipei Medical University, Taipei (TW)

(72) Inventor: Jian-Chiun Liou, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 50 days.

(21) Appl. No.: 16/902,300

(22) Filed: Jun. 16, 2020

(65) Prior Publication Data

US 2021/0077833 A1 Mar. 18, 2021

(30) Foreign Application Priority Data

Sep. 16, 2019 (TW) ................................. 108133280

(51) Int. Cl.
| | |
|---|---|
| *A61N 7/00* | (2006.01) |
| *G06F 3/04842* | (2022.01) |
| *A61B 8/00* | (2006.01) |
| *A61B 8/14* | (2006.01) |

(52) U.S. Cl.
CPC ................ *A61N 7/00* (2013.01); *A61B 8/145* (2013.01); *A61B 8/4455* (2013.01); *A61B 8/4494* (2013.01); *A61B 8/461* (2013.01); *A61B 8/467* (2013.01); *A61B 8/54* (2013.01); *A61B 8/565* (2013.01); *G06F 3/04842* (2013.01); *A61N 2007/0052* (2013.01); *A61N 2007/0078* (2013.01)

(58) Field of Classification Search
CPC .............. A61N 2007/0052; A61B 8/54; A61B 8/4494; A61B 8/467; A61B 8/461; G06F 3/04842; G06F 3/0482
See application file for complete search history.

(56) References Cited

U.S. PATENT DOCUMENTS

| | | | | | |
|---|---|---|---|---|---|
| 5,647,365 | A | * | 7/1997 | Abboud .............. | G01S 7/52046 600/447 |
| 6,736,779 | B1 | * | 5/2004 | Sano .................... | A61B 8/4494 600/447 |
| 10,537,304 | B2 | * | 1/2020 | Barthe .................. | A61B 8/465 |

(Continued)

FOREIGN PATENT DOCUMENTS

| | | |
|---|---|---|
| CN | 1112903 C | 7/2003 |
| CN | 101972154 A | 2/2011 |

(Continued)

*Primary Examiner* — Oommen Jacob
*Assistant Examiner* — Nyrobi Celestine
(74) *Attorney, Agent, or Firm* — Bacon & Thomas, PLLC

(57) ABSTRACT

A biological object image-capturing and treatment system includes a micro detection and treatment device. The micro detection and treatment device includes a plurality of signal transmitting and receiving elements arranged as an array, wherein adjacent at least two signal transmitting and receiving elements transmit signals or receive signals during different periods. When performing an image-capturing procedure, at least one signal transmitting and receiving element transmits a first power signal and, when performing a treatment procedure, at least one signal transmitting and receiving element transmits a second power signal, wherein a power of the first power signal is different from a power of the second power signal.

16 Claims, 12 Drawing Sheets

(56) References Cited

U.S. PATENT DOCUMENTS

| | | | |
|---|---|---|---|
| 10,603,014 B2* | 3/2020 | Sato | A61B 8/488 |
| 2004/0015079 A1 | 1/2004 | Berger et al. | |
| 2006/0235300 A1* | 10/2006 | Weng | A61B 17/0057 |
| | | | 600/439 |
| 2014/0243677 A1* | 8/2014 | Johnson | A61B 8/4444 |
| | | | 600/459 |
| 2014/0316269 A1* | 10/2014 | Zhang | A61N 7/02 |
| | | | 600/439 |
| 2017/0360413 A1* | 12/2017 | Rothberg | A61B 8/54 |
| 2021/0093897 A1* | 4/2021 | Zadicario | A61B 34/20 |

FOREIGN PATENT DOCUMENTS

| | | | |
|---|---|---|---|
| CN | 105310726 A | | 2/2016 |
| CN | 205306997 U | * | 6/2016 |
| CN | 205306997 U | | 6/2016 |
| CN | 106650201 A | | 5/2017 |

* cited by examiner

BIOLOGICAL OBJECT IMAGE-CAPTURING AND TREATMENT SYSTEM AND METHOD

BACKGROUND OF THE INVENTION

1. Field of the Invention

The present invention relates to a biological object image-capturing and treatment system with low noise and a method thereof.

2. Description of Related Art

Radiological medicine technology has been widely used in medical treatment behavior, such as ultrasound image-capturing technology or ultrasound therapy technology. Ultrasonic technology is provided with the following advantages: (1) it is less radioactive and therefore less harmful to the human body in comparison with other technologies; (2) its price is lower than other inspection techniques; (3) its equipment volume is smaller, and thus more flexible; and (4) the image-capturing speed is fast and the resolution is high. However, ultrasonic probes typically use piezoelectric transducers as signal transmitting and receiving components, and the materials of these transducers include piezoelectric polycrystalline ceramic materials, wherein the silver surface plated on the ceramic materials is connected to the electrode of the next transducer. Therefore, these ceramic materials are likely to produce resonance and, when adjacent transducers transmit or receive signals, the problem of signal interference often occurs.

In addition, there is currently no ultrasonic device into which the image-capturing function and the treatment function are integrated, and thus there are still deficiencies in terms of space occupation, production cost, or usage convenience.

Therefore, it is desirable to provide an improved biological object image-capturing and treatment system and method to mitigate and/or obviate the aforementioned problems.

SUMMARY OF THE INVENTION

The object of the present invention is to provide a biological object image-capturing and treatment system and method, with which not only the image-capturing function and the treatment function are integrated into the same device for reducing the occupied space of the device, but also special signal transmitting operation modes are employed to greatly reduce the interference between transmitting and receiving elements of each signal in the device, thereby significantly improving the signal accuracy.

In one aspect of the present invention, there is provided a biological object image-capturing and treatment system for performing an image-capturing procedure and a treatment procedure. The system comprises a micro detection and treatment device including a signal transmitting and receiving element array having a plurality of signal transmitting and receiving elements. The signal transmitting and receiving elements are set in a manner that adjacent at least two signal transmitting and receiving elements transmit signals or receive signals during different periods. When performing the image-capturing procedure, at least one signal transmitting and receiving element transmits a first power signal and, when performing the treatment procedure, at least one signal transmitting and receiving element transmits a second power signal, where the first power signal has a power different from that of the second power signal.

In another aspect of the present invention, there is provided a biological object image-capturing and treatment method performed by a biological object image-capturing and treatment system. The biological object image-capturing and treatment system comprises a micro detection and treatment device including a plurality of signal transmitting and receiving elements arranged in an array. The signal transmitting and receiving elements are set to enable adjacent at least two signal transmitting and receiving elements to transmit signals or receive signals during different periods. The method comprises the steps of: when performing an image-capturing procedure, transmitting a first power signal by at least one signal transmitting and receiving element; and when a treatment procedure, transmitting a second power signal by at least one signal transmitting and receiving element, wherein the first power signal has a power or a frequency different from that of the second power signal.

Other objects, advantages, and novel features of the invention will become more apparent from the following detailed description when taken in conjunction with the accompanying drawings.

DETAILED DESCRIPTION OF THE PREFERRED EMBODIMENT

The implementations of the present disclosure will be described with specific embodiments in the following description. A person skilled in the art will understand the advantages and the effects provided by the present disclosure. Different specific embodiments may be applicable according to the present disclosure.

Moreover, the orders such as "first", "second", and so on, in the specification and the claims are only used to distinguish the elements with the same name. They do not have their own specific meanings, do not necessarily mean that there is another element existing in addition to one element, and do not mean that there is a priority between one element and another element, or one step and another step.

Besides, in the present disclosure, the description such as "A happens when B happens" may refer to A happens before, when or after B happens, and it does not necessarily refer to A and B happen at the same time, except that a clear limitation is given. In the present disclosure, the description such as "A is disposed on B" refers to the corresponding locations of A and B, and it does not necessarily refer to the contact of A and B, except that a clear limitation is given. Moreover, the word "or" between the elements or their effects in the present disclosure means that the elements and the effects may exist individually or together.

In addition, in the present invention, the terms such as "connected", "electrically connected" or "coupled", unless otherwise emphasized, mean that the direct connection and the indirect connection are included. In addition, the terms "including", "including", "having", and "having" in this disclosure are all open descriptions, which are described first.

Furthermore, various embodiments of the biological object image-capturing and treatment system 1 of the present invention can be realized by a software program or an electronic circuit, and are not limited thereto.

Figure 1A:
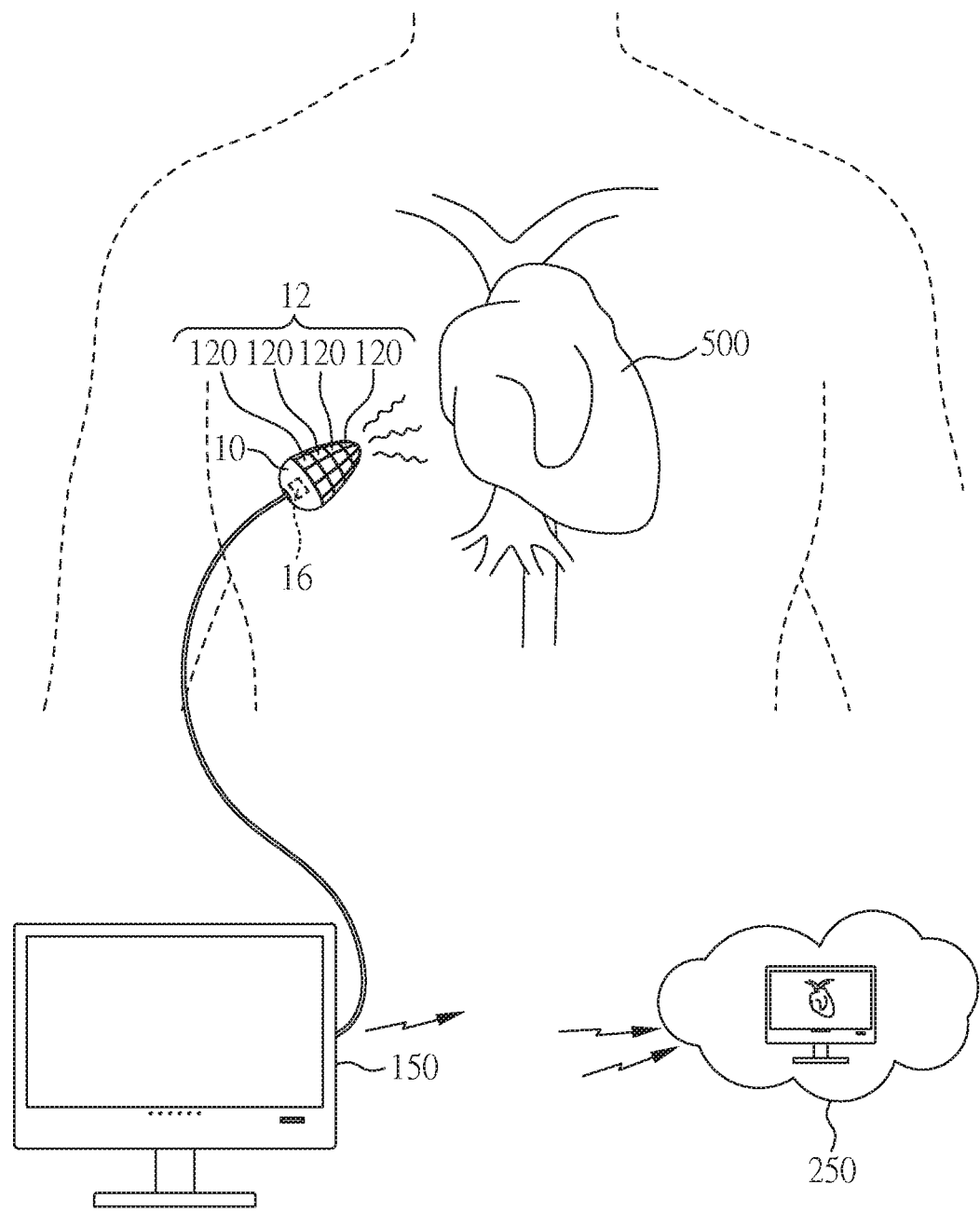
FIG. 1(A) is a schematic diagram illustrating the biological object image-capturing and treatment system according to an embodiment of the present invention.

FIG. 1(A) is a schematic diagram illustrating the biological object image-capturing and treatment system according to an embodiment of the present invention, wherein the biological object image-capturing and treatment system 1 may be used to perform an image-capturing procedure and a treatment procedure. As shown in FIG. 1, the biological object image-capturing and treatment system 1 at least includes one micro detection and treatment device 10. Further, the biological object image-capturing and treatment system 1 may further include a user operating device 150 and a cloud server 250. The micro detection and treatment device 10 includes a signal transmitting and receiving element array 12, and the signal transmitting and receiving element array 12 includes a plurality of signal transmitting and receiving elements 120 arranged in an array, wherein the signal transmitting and receiving elements 120 are configured in such a manner that: the adjacent at least two signal transmitting and receiving elements 120 respectively transmit signals or receive signals during different periods; that is, the period during which one signal transmitting and receiving element 120 transmits or receives signals does not overlap the period during which another signal transmitting and receiving element 120 transmits or receives signals. It should be noted that the "period" herein may be in a state of continuous time or instantaneous time. In addition, the micro detection and treatment device 10 may also include a controller 16 for controlling the operation of the micro detection and treatment device 10. In one embodiment, the micro detection and treatment device 10, the user operating device 150 and the cloud server 250 may transmit data to each other. The image-capturing procedure and the treatment procedure may be handled by separate subsystems, or the image-capturing procedure and the treatment procedure may be handled by a common system.

The micro detection and treatment device 10 is a medical detecting device, and has both an image-capturing function and a treatment function, wherein "micro" is defined as a size capable of being inserted into a human body. In one preferred embodiment, the micro detection and treatment device 10 is an ultrasonic detection and treatment device, and thus the signal transmitting and receiving element 120 is used for transmitting and receiving ultrasonic signals, but is not limited thereto. For convenience of description, the following description is given by taking the transmitting and receiving elements to transmit or receive ultrasonic signals as an example. When the biological object image-capturing and treatment system 1 performs an image-capturing process, the micro detection and treatment device 10 may transmit a first power signal to different positions of a target object 500 through the signal transmitting and receiving elements 120, and may receive signals reflected from different positions of the target object 500 through the signal transmitting and receiving elements 120. Furthermore, the reflected signals may be integrated through the user operating device 150 or the cloud server 250 so as to combine an ultrasonic image of the target object 500. When the biological object image-capturing and treatment system 1 performs a treatment procedure, the micro detection and treatment device 10 may transmit a second power signal to a specific position of the target object 500 through the signal transmitting and receiving elements 120, thereby treating the specific position of the target object 500, for example, ablation and other treatment behaviors. It should be noted that the first power signal and the second power signal have different powers or different frequencies. In one embodiment, the power of the first power signal is less than the power of the second power signal. In one embodiment, the frequency of the first power signal is higher than the frequency of the second power signal. In one embodiment, the power of the first power signal is 5 Watts and the frequency of the first power signal is 7 MHz, and the power of the second power signal is 20 Watts and the frequency of the second power signal is 20 kHz. As a result, the first power signal is suitable for object image-capturing, and the second power signal is suitable for treatment behavior such as ablation.

In addition, the micro detection and treatment device 10 may be, for example, an invasive medical device, so that it has a smaller volume than the existing handheld ultrasonic device. In FIG. 1(A), the target object 500 is exemplified by the heart of a human body, and the micro detection and treatment device 10 may be placed near the heart to perform image-capturing and treatment on the heart vascular wall, vein, and the like. In one embodiment, the micro detection and treatment device 10 may be of medical grade material suitable for placement into a human body. In one embodiment, at least a portion of the micro detection and treatment device 10 is a disposable component and can be replaced.

In one embodiment, the diameter of each of the signal transmitting and receiving elements 120 is equal to or smaller than 10000 micrometers (μm). In one embodiment, the diameter of each of the signal transmitting and receiving elements 120 is in a range of 4000 μm to 6000 μm (i.e. 4000 μm≤diameter≤6000 μm). In one embodiment, the diameter of each of the signal transmitting and receiving elements 120 is substantially 5000 μm. However, the invention is not limited thereto.

Since the micro detection and treatment device 10 of the invention can be inserted into the human body, compared to the prior technique, the micro detection and treatment device 10 is closer to a treatment target. Furthermore, because of having small volume, the signal transmitting and receiving elements 120 can provide more precise and accurate imaging distance, imaging depth and imaging width, so as to make a reflection of dose-response relationship more accurate.

Figure 1B:
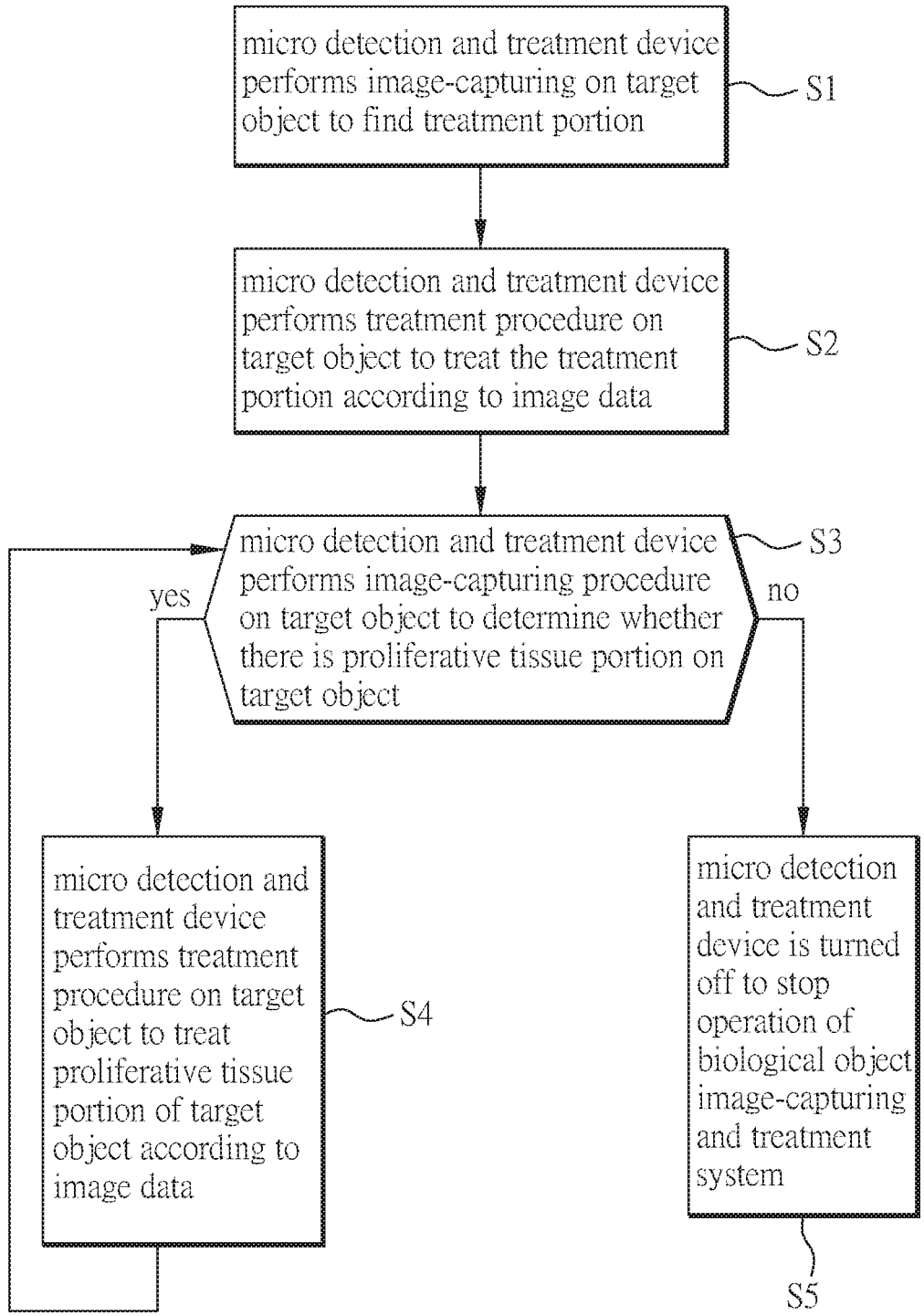
FIG. 1(B) is a flow chart illustrating the steps of the execution process of the biological object image-capturing and treatment system according to an embodiment of the present invention.

Besides, since the micro detection and treatment device 10 may perform an image-capturing procedure and a treatment procedure, the present invention may further perform special steps to achieve treatment and resection of the proliferative tissue at a specific position in the human body. FIG. 1(B) is a flow chart illustrating the steps of the execution process of the biological object image-capturing and treatment system according to an embodiment of the present invention, which depicts the processing steps of the micro detection and treatment device 10 for the treatment and resection of the proliferative tissue. With reference to both FIG. 1(A) and FIG. 1(B), step S is first executed, in which the micro detection and treatment device 10 is used to perform image-capturing on the target object 500 to find a treatment portion on the target object 500, whereby the user (for example, a doctor) may find the portion to be treated. Thereafter, step S2 is executed, in which the micro detection and treatment device 10 is used to perform a treatment procedure on the target object 500 to treat the treatment portion of the target object 500 according to the image data obtained in step S1, thereby treating the portion to be treated. Then, step S3 is executed, in which the micro detection and treatment device 10 is used again to perform an image-capturing procedure on the target object 500 to determine whether there is a proliferative tissue portion on the target object 500, thereby allowing the user to find the proliferative tissue portion. When a proliferative tissue portion exists, step S4 is executed, in which the micro detection and treatment device 10 is used again to perform a treatment procedure on the target object 500 to treat the proliferative tissue portion of the target object 500 according to the image data obtained in step S3, whereby the proliferative tissue portion can be treated. Furthermore, when the treatment procedure is completed, step S3 is executed again and, after execution of the steps S3 and S4 for several times, the proliferative tissue portion will be fully treated and resected. Therefore, when the proliferative tissue portion does not exist, step S5 is executed, in which the micro detection and treatment device 10 is turned off to stop the operation of the biological object image-capturing and treatment system, thereby completing the treatment and resection of the proliferative tissue portion at the specific position in the human body.

Please refer to FIG. 1(A) again. The user operating device 150 may be connected to the micro detection and treatment device 10 in a manner of wired transmission or wireless transmission, whereby the user may transmit a control command to the micro detection and treatment device 10 through the user operating device 150. In one embodiment, the user operating device 150 may be various electronic devices with a microprocessor, such as a desktop computer, a notebook computer, a smart phone, a tablet computer, a touch device, and the like, and is not limited thereto. More details regarding the user operating device 150 will be explained in more detail in the subsequent paragraphs with reference to FIG. 3(B).

The cloud server 250 may perform data backup or data processing. In one embodiment, the micro detection and treatment device 10 may transmit/receive data to/from the cloud server 250 in a manner of wireless transmission if it is provided with a wireless transmission device. In another embodiment, the micro detection and treatment device 10 may also first transmit data to the user operating device 150 in a wired transmission manner, and then the user operating device 150 transmits the data to the cloud server 250. The present invention is not limited thereto. In one embodiment, after the signal transmitting and receiving elements 120 receive the reflected signal from the target object 500, instead of performing image formation, the micro detection and treatment device 10 transfers the data to the user operating device 150 or the cloud server 250 to perform image formation.

Next, the detailed structure of the controller 16 of the micro detection and treatment device 10 will be described.

Figure 2:
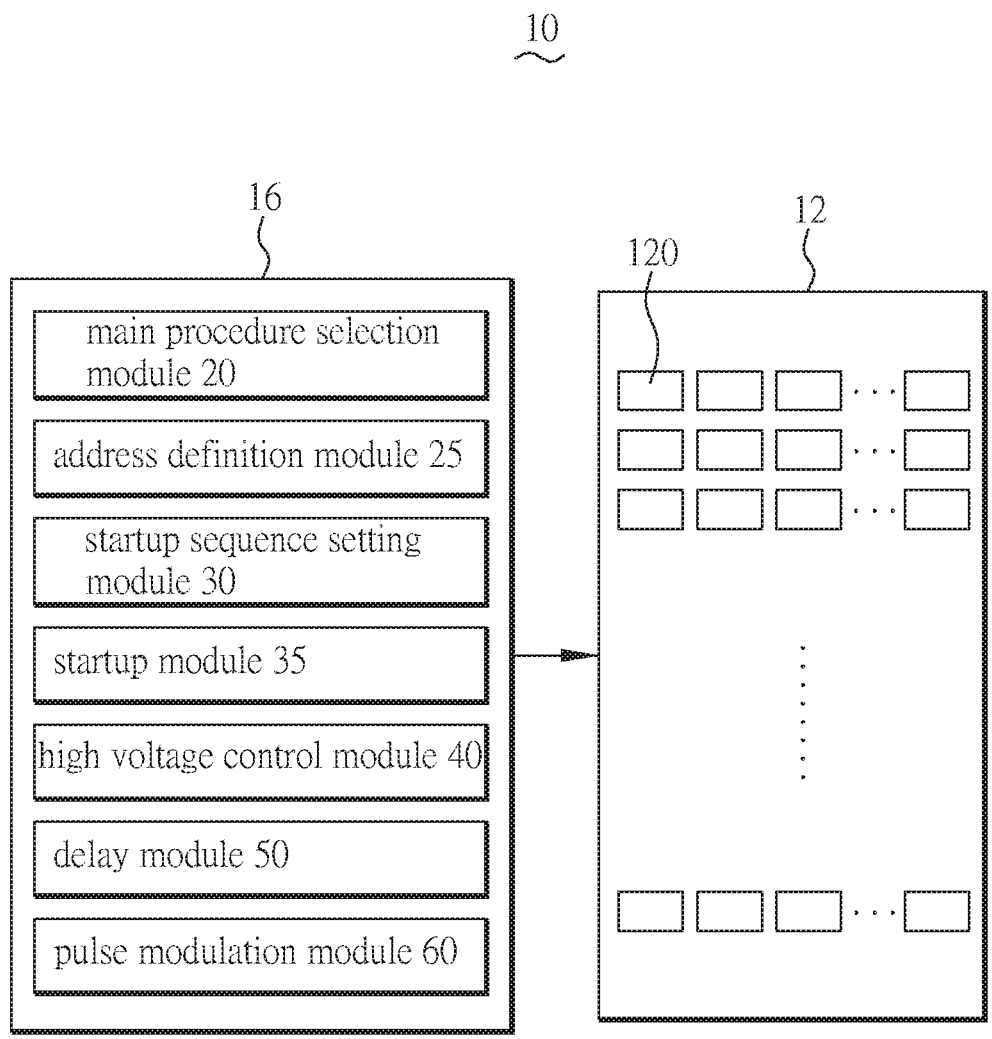
FIG. 2 schematically illustrates a controller of a micro detection and treatment device according to an embodiment of the present invention.

FIG. 2 schematically illustrates a controller 16 of a micro detection and treatment device 10 according to an embodiment of the present invention. With reference to both FIG. 1(A) and FIG. 2, the controller 16 is disposed inside the micro detection and treatment device 10. The controller 16 may be coupled to the signal transmitting and receiving element array 12 to control the operation of the signal transmitting and receiving elements 120. In one embodiment, the controller 16 may include a main procedure selection module 20, an address definition module 25, a startup sequence setting module 30, and a startup module 35. Alternatively, the micro detection and treatment device 10 may further include a high voltage control module 40, a delay module 50, and a pulse modulation module 60. The type and the quantity of the aforementioned modules are only examples and are not limited, and may be arbitrarily increased or decreased according to the needs of the user. In addition, the modules may be arbitrarily connected or integrated as long as they can be realized. In one embodiment, the controller 16 is a control chip, and the function of each module can be implemented by at least one digit logic circuit or computer program, and is not limited thereto.

First, the main procedure selection module 20 is described. The main procedure selection module 20 may be used to execute an image-capturing procedure or a treatment procedure. For example, the main procedure selection module 20 selects the image-capturing procedure or the treatment procedure for execution according to a predetermined command or a control command of the user operating device 150, and further controls the signal transmitting and receiving element array 12 to transmit the first power signal or the second power signal. In addition, in one embodiment, the main procedure selection module 20 may further select different image-capturing modes for execution. For example, the image-capturing procedure may include a first image-capturing mode, a second image-capturing mode, a third image-capturing mode and a fourth image-capturing mode, and the treatment procedure may include a first treatment mode and a second treatment mode, which will be described in order in the following.

In one embodiment, the first image capturing mode is set to transmit the first power signal to different positions of the target object 500 by using a single signal transmitting and receiving element 120, and receive reflection signals reflected from the different positions of the target object 500 at different time points by using a single signal transmitting and receiving element 120. In this embodiment, the signal transmitting and receiving element that transmits the first power signal is not limited to be the same as the signal transmitting and receiving element that receives the reflection signals. In addition, since a single signal transmitting and receiving element 120 must transmit signals toward different positions of the target object 500, the signal transmitting and receiving element array 12 is designed to be rotatable, but is not limited thereto.

In one embodiment, the second image-capturing mode is set to transmit the first power signal to different positions of the target object 500 by using a plurality of signal transmitting and receiving elements 120, and receive reflection signals reflected from the different positions of the target object 500 at different time points by using a single signal transmitting and receiving element 120. In this embodiment, between the signal transmitting and receiving elements 120 that transmit signals, there is an interval of at least one signal transmitting and receiving element, and thus they are not adjacent to each other. In addition, signals may be transmitted simultaneously or sequentially. In addition, the signal transmitting and receiving elements 120 that transmit signals may also be used to receive signals.

In one embodiment, the third image-capturing mode is set to transmit the first power signal to different positions of the target object 500 by using a single signal transmitting and receiving element 120, and receive reflection signals reflected from the different positions of the target object 500 at different time points by using a plurality of signal transmitting and receiving elements 120. Between the signal transmitting and receiving elements 120 that receive signals, there is an interval of at least one signal transmitting and receiving element, and thus they are not adjacent to each other. In addition, the signal transmitting and receiving element 120 that transmits signals may also be used to receive signals.

In one embodiment, the fourth image-capturing mode is set to transmit the first power signal to different positions of the target object 500 by using a plurality of single signal transmitting and receiving elements 120, and receive reflection signals reflected from the different positions of the target object 500 at different time points by using a plurality of signal transmitting and receiving elements 120. In this embodiment, the signal transmitting and receiving elements 120 that transmit signals are not adjacent to each other, and the signal transmitting and receiving elements 120 that receive signals are also not adjacent to each other. In this embodiment, the signal transmitting and receiving elements 120 that transmit signals may not be in consistency with the signal transmitting and receiving elements 120 that receive signals. In addition, signals can be transmitted simultaneously or sequentially.

In one embodiment, the first treatment mode is set to transmit the second power signal to different positions of the target object 500 by using a single signal transmitting and receiving element 120. It is noted that, when the first treatment mode is executed, the second power signal from the single signal transmitting and receiving element 120 does not need to be focused.

In one embodiment, the second treatment mode is set to transmit the second power signal to the different positions of the target object 500 by using a plurality of signal transmitting and receiving elements 120. In this embodiment, the signal transmitting and receiving elements 120 that transmit signals are not adjacent to each other. In addition, signals can be transmitted simultaneously or sequentially. It is noted that, when the second treatment mode is executed, the second power signal from the single signal transmitting and receiving elements 120 do not need to be focused.

Next, the address definition module 25 is described. The address definition module 25 may define the address parameter of each signal transmitting and receiving element 120. For example, if the signal transmitting and receiving element array 12 has 64 signal transmitting and receiving elements 120, there are also 64 address parameters, and each signal transmitting and receiving element 120 corresponds to one address parameter.

Next, the startup sequence setting module 30 is described. When using a plurality of signal transmitting and receiving elements 120 to transmit or receive signals, in order to avoid interference generated between the adjacent signal transmitting and receiving elements in operation, the startup sequence setting module 30 may control the signal transmitting and receiving elements 120 to perform a specific startup sequence mode so as to shift the transmitting and receiving timing of the adjacent signal transmitting and receiving elements 120. The specific startup sequence mode is provided to sequentially or simultaneously start the signal transmitting and receiving elements in a manner of spacing N signal transmitting and receiving elements 120, wherein N is a positive integer of 1 or more ($1 \leq N$), and N is smaller than the total number of the signal transmitting and receiving elements 120.

In one embodiment, the startup sequence setting module 30 may execute a first startup sequence mode, wherein the signal transmitting and receiving elements 120 are sequentially or simultaneously started in a manner of spacing one signal transmitting and receiving element 120. Under this startup sequence, the signal transmitting and receiving elements of odd address parameter are started sequentially or simultaneously to receive or transmit signals. When the signal transmitting and receiving elements of odd address parameter complete the signal receiving or transmitting, the signal transmitting and receiving elements of even address parameter will start receiving or transmitting signals sequentially or simultaneously. In addition, it is also possible to first start the operation by using the signal transmitting and receiving element of even address parameter.

In one embodiment, the startup sequence setting module 30 may execute a second startup sequence mode, wherein the signal transmitting and receiving elements 120 are sequentially or simultaneously started in a manner of spacing two signal transmitting and receiving elements 120. Under this startup sequence, the signal transmitting and receiving elements with address parameters of 1, 4, 7, 10 and so on are started sequentially or simultaneously (for performing signal receiving or transmitting). Then, the signal transmitting and receiving elements with address parameters of 2, 5, 8 11 and so on are started sequentially or simultaneously, and subsequently the signal transmitting and receiving elements with the address parameters of 3, 6, 9, 12 and so on are started sequentially or simultaneously.

In one embodiment, the startup sequence setting module 30 may perform a third startup sequence mode, wherein the signal transmitting and receiving elements 120 are sequentially or simultaneously started in a manner of spacing three signal transmitting and receiving elements 120. Under this startup sequence, the signal transmitting and receiving elements with address parameters of 1, 5, 9, 13 and so on are started sequentially or simultaneously (for performing signal receiving or transmitting), and then the signal transmitting and receiving elements with address parameters of 2, 6, 10, 14 and so on are started sequentially or simultaneously. Subsequently, the signal transmitting and receiving elements with address parameters of 3, 7, 11, 15 and so on are started sequentially or simultaneously, and then the signal transmitting and receiving elements with address parameters of 4, 8, 12, 16 and so on are started sequentially or simultaneously.

On this basis, there N types of startup sequence modes are available for execution to prevent adjacent 1 to N signal transmitting and receiving elements 120 from performing signal transmitting or receiving during the same period, thereby avoiding interference problem among the ultrasonic signals. The N types of startup sequence modes may be suitable for signal transmitting or receiving in the image-capturing procedure or the treatment procedure.

Next, the startup module 35 is described. The startup module 35 may generate a plurality of startup signals according to the startup sequence mode set by the startup sequence setting module 30, wherein the startup signals correspond to the address parameters corresponding to the startup sequence mode, and are used to actually start the signal transmitting and receiving elements 120 corresponding to the address parameters. For example, when the second startup sequence mode is set, the startup module transmits the startup signal to the signal transmitting and receiving elements 120 corresponding to the address parameters according to the startup sequence of the second startup sequence mode (for example, first starting the address parameters of 1, 4, 7, 10 and so on, and then starting the address parameters of 2, 5, 8, 11 and so on), so as to start the signal transmitting and receiving elements 120 for performing signal transmitting or receiving.

Next, the high voltage control module 40 is described. In one embodiment, since the voltage required for the signal transmitting and receiving elements 120 to transmit the ultrasonic signals is as high as 40 volts (40 V) or more, a high voltage must be applied to drive the signal transmitting and receiving elements 120 through the high voltage control module 40, and thus the high voltage control module 40 can be used to control whether the signal transmitting and receiving elements 120 actually transmit the ultrasonic signals. With this feature, the high voltage control module 40 may also be used to assist in avoiding interference caused by adjacent at least two signal transmitting and receiving elements. For example, the high voltage control module 40 may detect whether the adjacent at least two signal transmitting and receiving elements 120 receive the startup signal at the same time or in a specific time. If yes, the high voltage control module 40 may output a disable signal (for example, "0") for the at least two signal transmitting and receiving elements 120; that is, no high voltage is applied to the at least two signal transmitting and receiving elements 120. If not, the high voltage control module 40 may output an enable signal (for example, "1") for the at least two signal transmitting and receiving elements 120; that is, a high voltage is applied to the at least two signal transmitting and receiving elements 120. However, the invention is not limited thereto. In one embodiment, the high voltage control module 40 is a hardware circuit; while the invention is not limited thereto.

Next, the delay module 50 is described. In one embodiment, the delay module 50 may control the signal transmitting periods of the adjacent at least two signal transmitting and receiving elements 120 to have a time interval ($\Delta T$) in advance, so that the adjacent two signal transmitting and receiving elements 120 will not perform signal transmitting and receiving during the same period regardless of the startup sequence mode.

Next, the pulse modulation module 60 is described. In one embodiment, because the fault of the controller 16 caused by certain factors during the manufacturing process may result in the micro detection and treatment device 10 failing to output the correct power, the first power signal or the second power signal may be affected, resulting in a negative influence to the image-capturing or treatment quality. Therefore, the controller 16 may be configured with a pulse modulation module 60 for performing pulse width modulation on the signals inputted to the controller 16 or the signals outputted from the controller 16 so as to correct and enhance the signals, thereby allowing the micro detection and treatment device 10 to output the power of stable ultrasonic signal. However, the invention is not limited thereto.

Figure 3A:
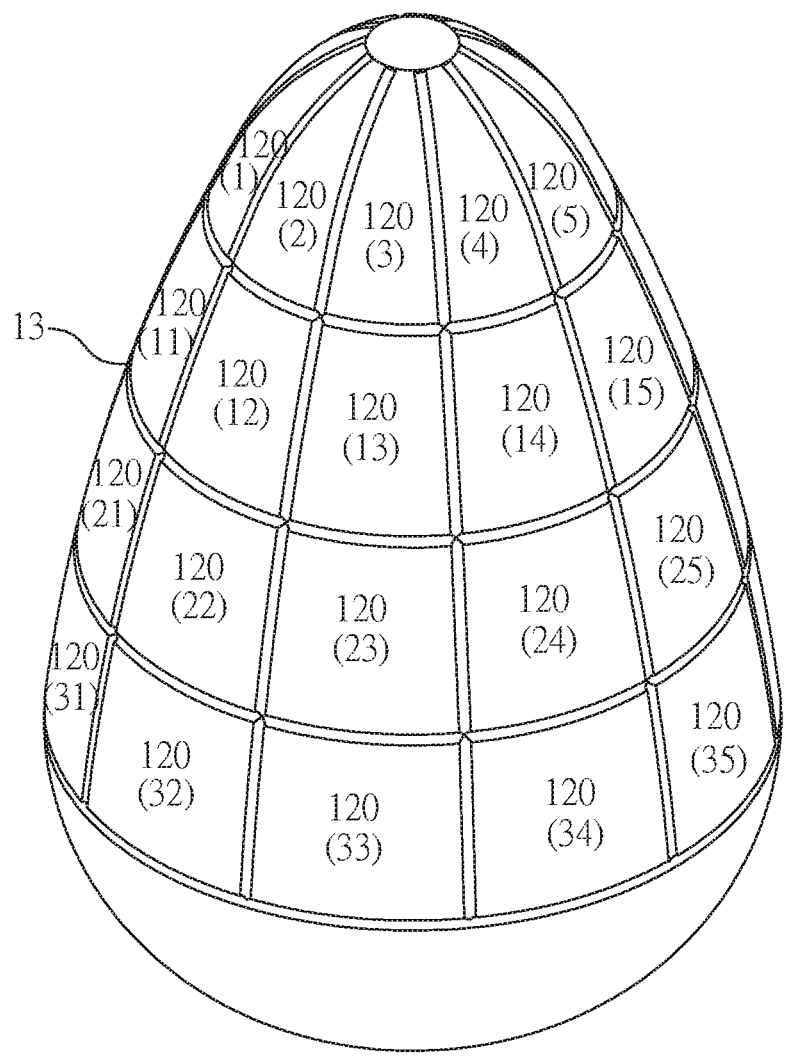
FIG. 3(A) schematically illustrates a signal transmitting and receiving element array according to an embodiment of the present invention.

Next, the detailed features of the signal transmitting and receiving element array 12 are described. FIG. 3(A) schematically illustrates a signal transmitting and receiving element array according to an embodiment of the present invention. As shown in FIG. 3(A), the micro detection and treatment device 10 may have a cylindrical probe portion 13, and the signal transmitting and receiving element array 12 surrounds the probe portion 13 by, for example, 360 degrees. In one example, the signal transmitting and receiving element array 12 may be provided with 64 signal transmitting and receiving elements 120, which are equally arranged into an array and are divided into 4 rows, each row having 16 elements, each element being assigned with an address parameter (shown as brackets and numbers in the figure), but are not limited thereto. In other embodiments, the signal transmitting and receiving element array 12 may also be provided with other quantity of signal transmitting and receiving elements 120, such as 16, 32, 128 or 256. In one embodiment, the signal transmitting and receiving element array 12 and the probe portion 13 may be provided with a pivoting mechanism. Therefore, the signal transmitting and receiving element array 12 is rotatable relative to the probe portion 13, but is not limited thereto. In one embodiment, the material of the signal transmitting and receiving element 120 is PZT (lead-zirconate-titanate), but is not limited thereto. In one embodiment, each of the signal transmitting and receiving elements 120 has a size of at least 1.0 mm×1.0 mm, but is not limited thereto. In addition, in one embodiment, intervals may be provided between different rows, and thus each row may be regarded as a ring, but is not limited.

Figure 3B:
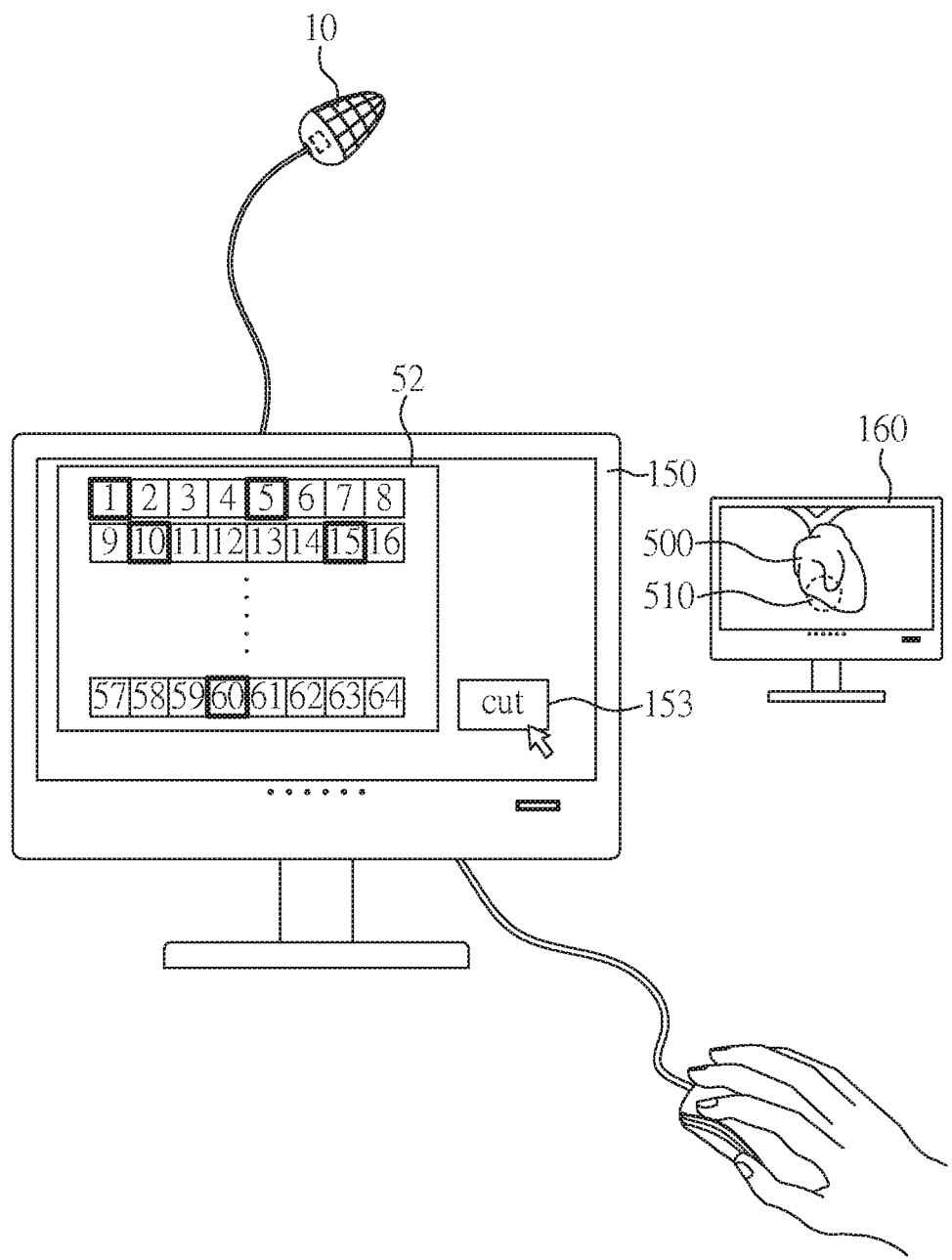
FIG. 3(B) schematically illustrates a user operating device corresponding to the signal transmitting and receiving element array according to an embodiment of the present invention.

FIG. 3(B) schematically illustrates a user operating device corresponding to the signal transmitting and receiving element array 12 according to an embodiment of the present invention. With reference to FIG. 3(B) and FIGS. 1(A) to 3(A), in one embodiment, the image (target object 500 and treatment portion 510) obtained by the image-capturing procedure may be displayed on a display device 160, and the address parameter of each signal transmitting and receiving element 120 may correspond to a lookup table. The user operating device 150 may be provided with a display area 52 for correspondingly displaying each address parameter according to the lookup table, and presenting each address parameter in a form of user-selectable key. Therefore, the user may directly select the desired signal transmitting and receiving element 120 on the user operating device 150 according to the treatment portion 510 of the target object 500 and, after the selection, uses a startup button 153 on the user operating device 150 to transmit a control command to the micro detection and treatment device 10. In addition, in another embodiment, the display device 160 can be integrated into the user operating device 150; that is, the image obtained by the image-capturing procedure can be displayed in the display area 52 at the same time with the address parameter of each signal transmitting and receiving element 120. However, the present invention is not limited thereto.

In one embodiment, when the micro detection and treatment device transmits the "treatment signal (e.g. the second power signal)", the display device 160 simultaneously displays the image-capturing of the treatment target, and the change of the treatment target can be presented. Thus, various treatment parameters (e.g. the treatment signal power, treatment period, etc.) can be adjusted in real time. In addition, since the display device 160 can display image-capturing in real time during the treatment process, the user or the micro detection and treatment device 10 can obtain the actual treatment area through the ratio conversion of the ultrasound image (e.g. correlation coefficient), and then determine whether to adjust the treatment position. In one embodiment, "simultaneously displaying the ultrasound images" can be achieved at least by: using the energy reflected from the treatment location to execute the piezoelectricity image-capturing on the same axis space of the treatment location.

In one embodiment, since the display device 160 can display images in real time during the treatment process, the biological object image-capturing and treatment system 1 of the present invention can provide a function of monitoring the treatment process. In addition, since the monitoring function can be performed before or during the treatment process, the accuracy of the treatment can be improved.

The user operating device 150 may have various implementations. FIGS. 3(C) to 3(H) schematically illustrate various implementations of the user operating device 150 according to another embodiment of the present invention, and please refer to FIGS. 1(A) to 3(B) at the same time.

Figure 3C:
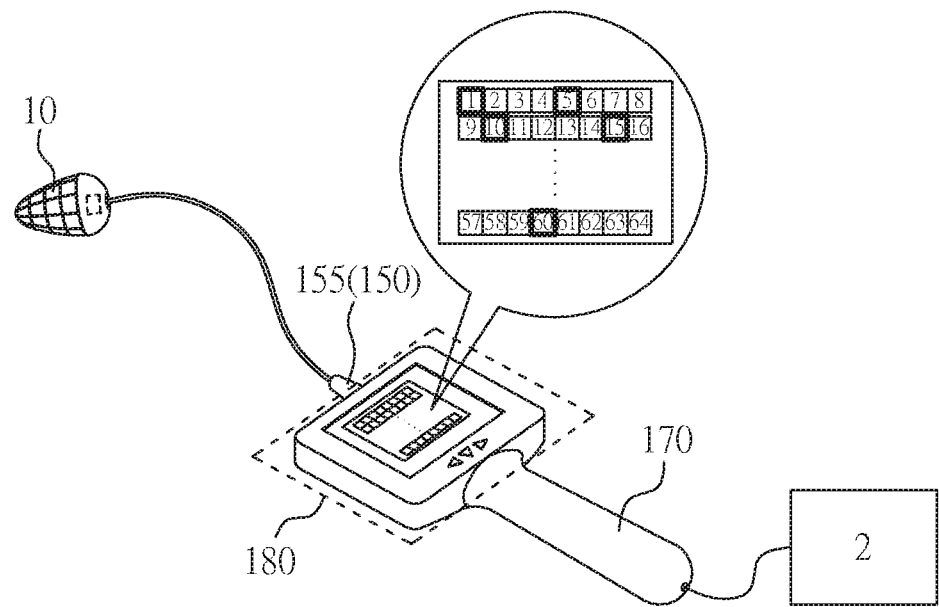
FIG. 3(C) schematically illustrates an implementation of the user operating device according to another embodiment of the present invention.

With reference to FIG. 3(C), the user operating device 150 can be integrated with a handle 170 to form a handheld user operating device 155, both of which can be integrated in an integrally formed manner. In this embodiment, the handle 170 is provided with a button area 180. The button area 180 includes a plurality of buttons corresponding to the signal transmitting and receiving elements 120 for allowing the user to select the signal transmitting and receiving element 120 to be used. As with the example of FIG. 3(B), the address parameters of each of the signal transmitting and receiving elements 120 may correspond to a look table, and each of the address parameters may be selected by the button 170. In one embodiment, the button area 180 may be presented in various manners, such as selectable buttons in the display screen, physical array buttons, physical rotary buttons, and the like, and is not limited thereto. Furthermore, in this embodiment, the handheld user operating device 155 is combined with a subsystem 2 responsible for the image-capturing procedure in the biological object image-capturing and treatment system 1, and thus only supports the function of the image-capturing procedure.

Figure 3D:
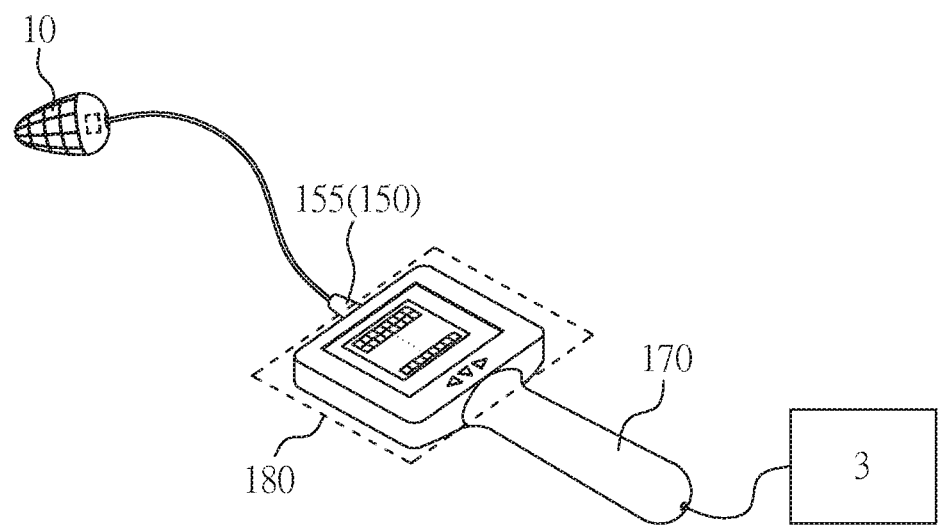
FIG. 3(D) schematically illustrates an implementation of the user operating device according to another embodiment of the present invention.

With reference to FIG. 3(D), the user operating device 150 may also be integrated with a handle 170 to form a handheld user operating device 155, wherein the details of the handheld user operating device 155 are substantially similar to FIG. 3(C) and thus a detained description therefor is deemed unnecessary. It should be noted that, in this embodiment, the handheld user operating device 155 is combined with a subsystem 3 responsible for the treatment procedure in the biological object image-capturing and treatment system 1, and thus only supports the function of the treatment procedure.

Figure 3E:
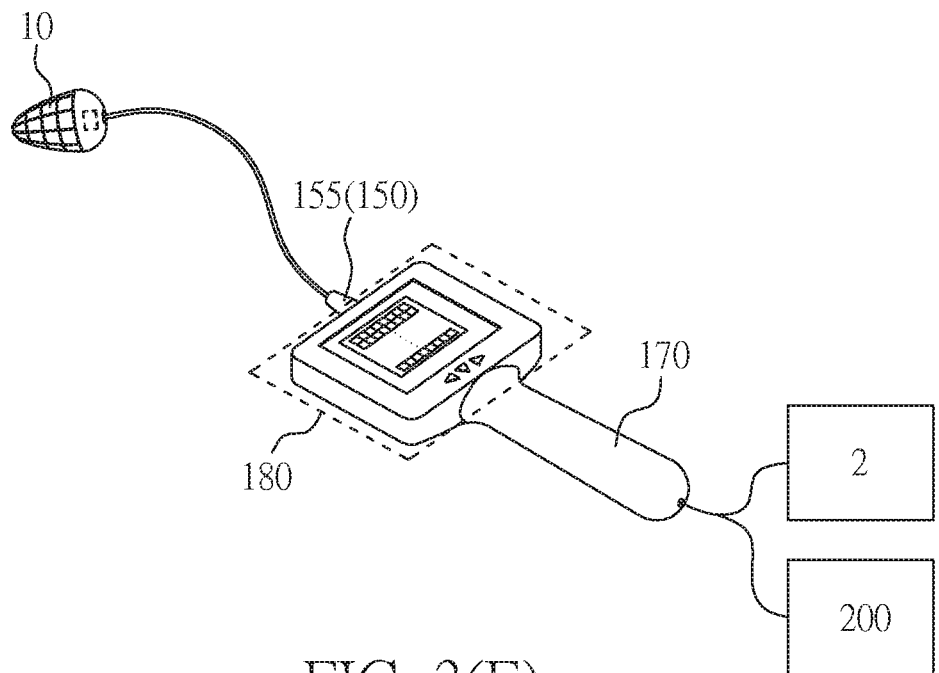
FIG. 3(E) schematically illustrates an implementation of the user operating device according to another embodiment of the present invention.

With reference to FIG. 3(E), the user operating device 150 may also be integrated with the handle 170 to form a handheld user operating device 155, wherein the details of the handheld user operating device 155 are substantially similar to FIG. 3(C) and thus a detailed description therefor is deemed unnecessary. It should be noted that, in this embodiment, the handheld user operating device 155 is combined with a conventional treatment system (RF ablation) 200 and a subsystem 2 responsible for the image-capturing procedure in the biological object image-capturing and treatment system 1, and thus it is able to support the function of the image-capturing procedure and the function of the conventional treatment system 200, wherein the conventional treatment system 200 and the subsystem 2 responsible for the image-capturing procedure are two independent systems, not a common system.

Figure 3F:
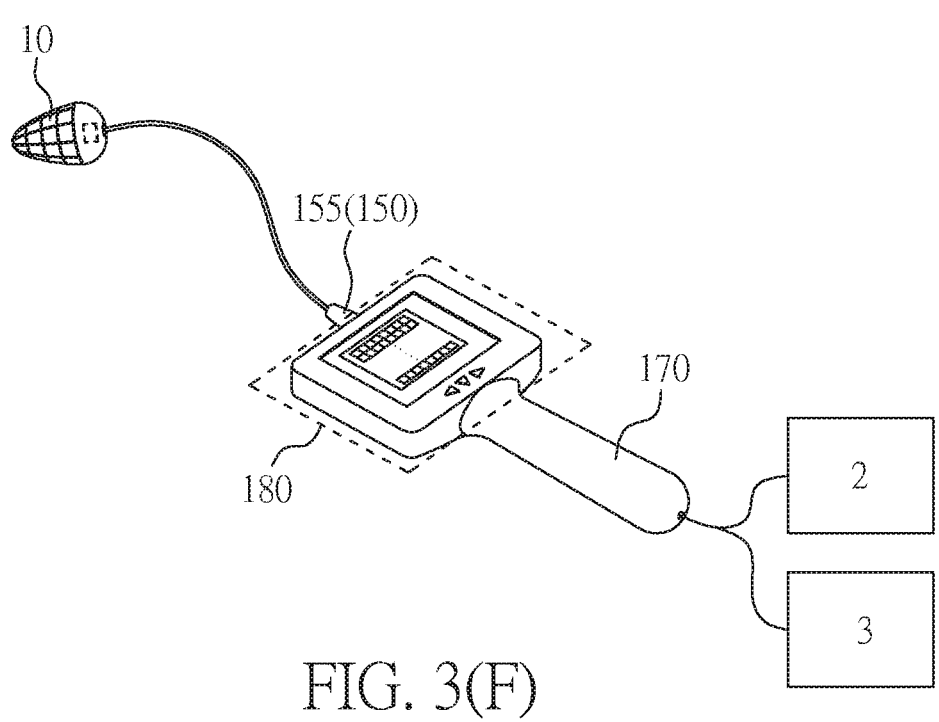
FIG. 3(F) schematically illustrates an implementation of the user operating device according to another embodiment of the present invention.

With reference to FIG. 3(F), the user operating device 150 may also be integrated with the handle 170 to form a handheld user operating device 155, wherein the details of the handheld user operating device 155 are substantially similar to FIG. 3(C) and thus a detailed description therefor is deemed unnecessary. It should be noted that, in this embodiment, the handheld user operating device 155 is combined with the subsystem 2 responsible for the image-capturing procedure and the subsystem 3 for the treatment procedure in the biological object image-capturing and treatment system 1, and thus simultaneously supports the functions of the image-capturing procedure and the treatment procedure of the biological object image-capturing and treatment system 1, wherein the subsystem 2 responsible for the image-capturing procedure and the subsystem 3 responsible for the treatment procedure are two independent systems, not a common system.

Figure 3G:
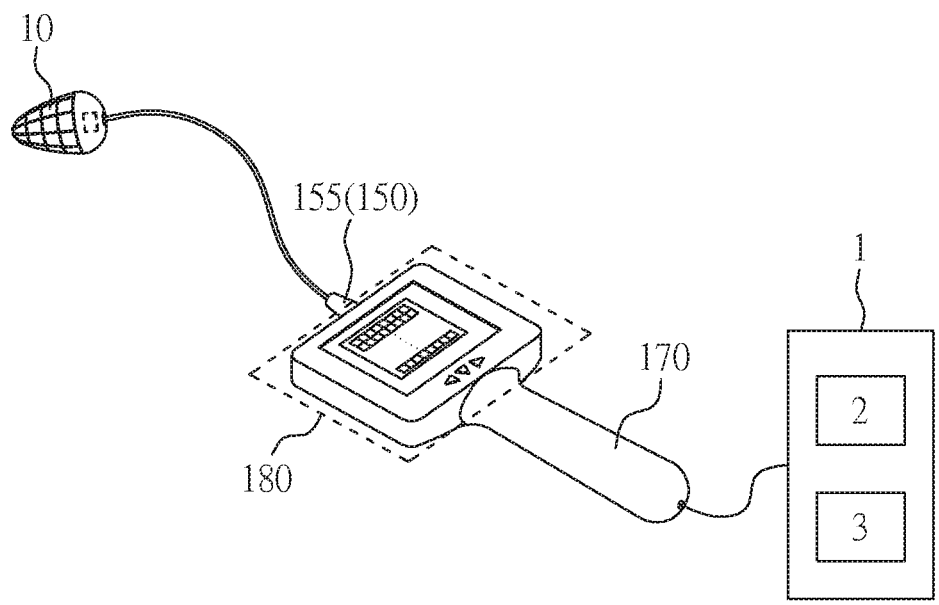
FIG. 3(G) schematically illustrates an implementation of the user operating device according to another embodiment of the present invention.

With reference to FIG. 3(G), the user operating device 150 may also be integrated with a handle 170 to form a handheld user operating device 155, wherein the details of the handheld user operating device 155 are substantially similar to FIG. 3(C) and thus a detailed description therefor is deemed unnecessary. It should be noted that, in this embodiment, the handheld user operating device 155 is combined with the biological object image-capturing and treatment system 1, and thus simultaneously supports the functions of the image-capturing procedure and the treatment procedure of the biological object image-capturing and treatment system 1 (i.e., the subsystem 2 responsible for the image-capturing procedure and the subsystem 3 responsible for the treatment procedure are a common system).

Figure 3H:
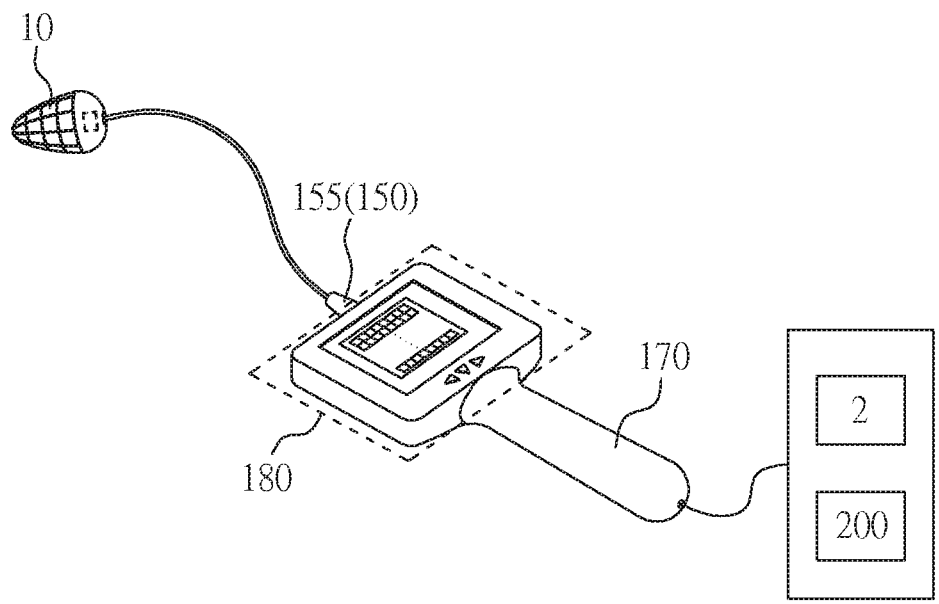
FIG. 3(H) schematically illustrates an implementation of the user operating device according to another embodiment of the present invention.

With reference to FIG. 3(H), the user operating device 150 may also be integrated with the handle 170 to form a handheld user operating device 155, wherein the details of the handheld user operating device 155 are substantially similar to FIG. 3(C) and thus a detailed description therefor is deemed unnecessary. It should be noted that, in this embodiment, the handheld user operating device 155 is combined with a conventional treatment system 200 and a subsystem 2 responsible for the image-capturing procedure in the biological object image-capturing and treatment system 1, and thus supports the function of the conventional treatment system 200 and the function of the image-capturing procedure, wherein the conventional treatment system 200 and the subsystem 2 responsible for the image-capturing procedure are a common system.

Figure 3I:
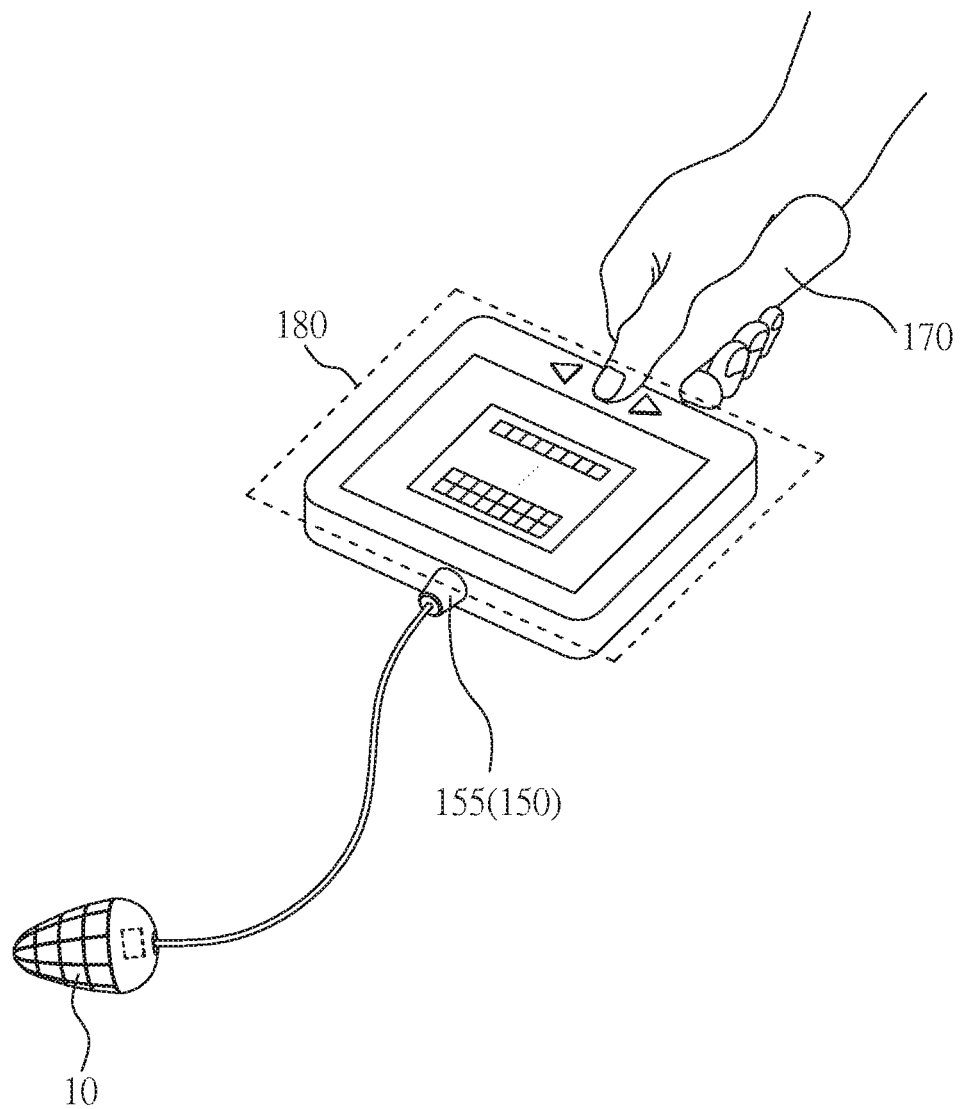
FIG. 3(I) schematically illustrates the use of the handheld user operating device of FIG. 3 (C) to FIG. 3(H)

FIG. 3(I) schematically illustrates the use of the handheld user operating device 155 of FIG. 3 (C) to FIG. 3(H). As shown in FIG. 3(I), in one embodiment, the user may hold the handle 170 with one hand and press the button with the thumb to operate the handheld user operating device 155. As a result, it is able to provide the convenience in the use and the lightweight effect of the device itself.

Next, the detailed process of the image-capturing procedure and the treatment procedure is described with reference to FIGS. 4 and 5, and please refer to FIGS. 1 to 3 at the same time.

Figure 4:
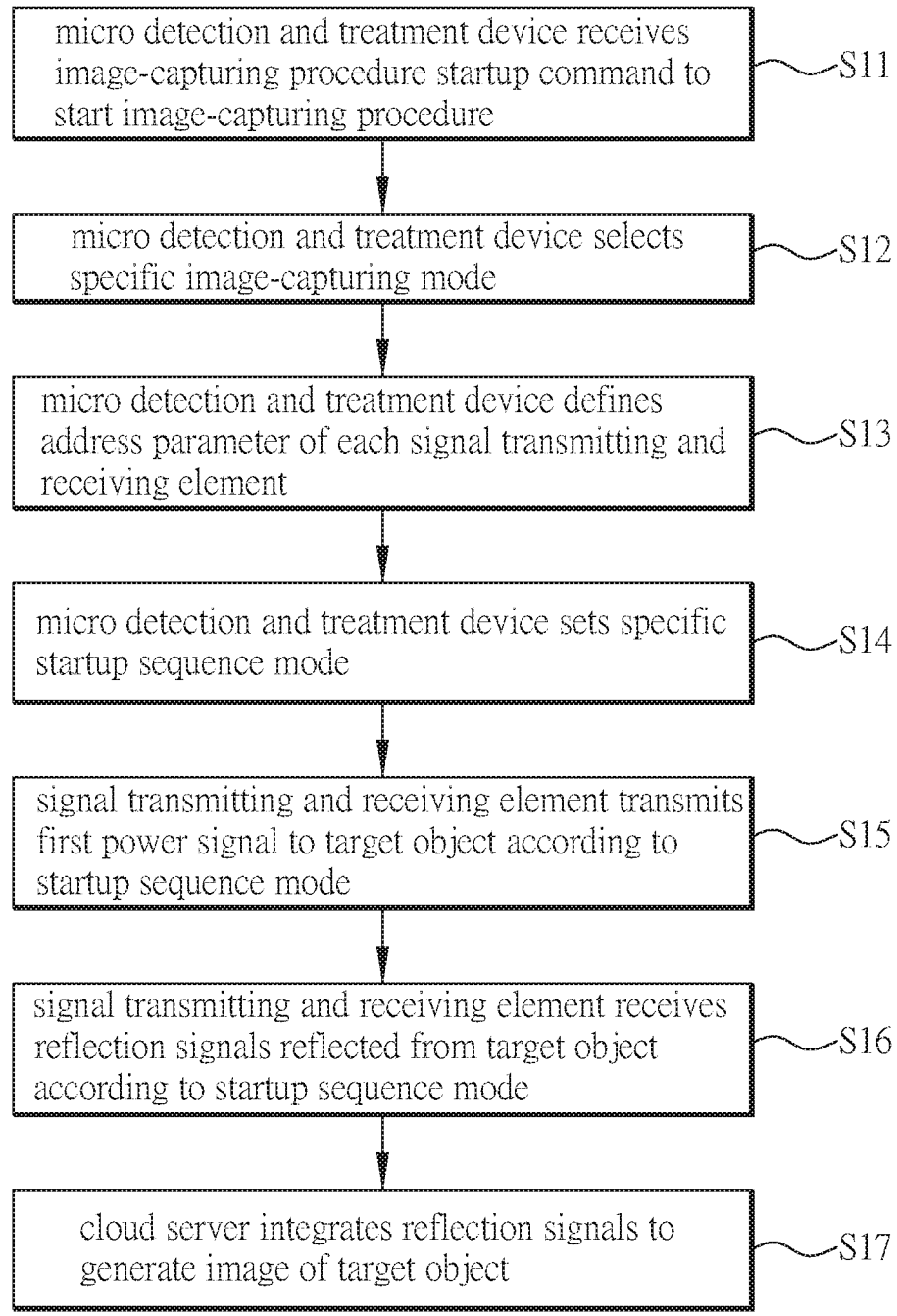
FIG. 4 is a flow chart illustrating the steps of an image-capturing procedure of the biological object image-capturing and treatment method according to an embodiment of the present invention.

FIG. 4 is a flow chart illustrating the steps of an image-capturing procedure of the biological object image-capturing and treatment method according to an embodiment of the present invention, which is performed by the biological object image-capturing and treatment system 1. In one embodiment, the method is performed with the micro detection and treatment device 10 disposed adjacent to the target object 500. First, step S11 is executed, in which the micro detection and treatment device 10 receives an image-capturing procedure startup command to start the image-capturing procedure. Then, step S12 is executed, in which the micro detection and treatment device 10 selects a specific image-capturing mode. Then, step S13 is executed, in which the micro detection and treatment device 10 defines the address parameter of each of the signal transmitting and receiving elements 120. Then, step S14 is executed, in which the micro detection and treatment device 10 sets a specific startup sequence mode. Then, step S15 is executed, in which the signal transmitting and receiving element 120 corresponding to the specific address parameter transmits (sequentially or simultaneously transmits) the first power signal to the target object 500 according to the startup sequence mode. Then, step S16 is executed, in which the signal transmitting and receiving element 120 corresponding to the specific address parameter receives (sequentially or simultaneously receives) the reflection signals reflected from the target object 500 according to the startup sequence mode. Then, step S17 is executed, in which the cloud server 250 integrates the reflection signals to generate an image of the target object 500.

In step S11, the image-capturing procedure startup command may be a control command transmitted by the user through the user operation device 150, or may be a predetermined command built in the controller 16 of the micro detection and treatment device 10. In one embodiment, the user may start the micro detection and treatment device 10 through the user operating device 150 and select to perform an image-capturing procedure or a treatment procedure. In another embodiment, the micro detection and treatment device 10 is predetermined to perform the image-capturing procedure first when the power is turned on. However, the present invention is not limited thereto.

In step S12, the main procedure selection module 20 may select to perform the first image-capturing mode, the second image-capturing mode, the third image-capturing mode or the fourth image-capturing mode, thereby determining whether to transmit the first power signal by one or a plurality of signal transmitting and receiving elements 120 or to receive the reflection signals by one or a plurality of signal transmitting and receiving elements 120. In one embodiment, the main procedure selection module 20 can select one of the image-capturing modes according to the control command transmitted by the user. In another embodiment, the main procedure selection module 20 may select one of the image-capturing modes according to a predetermined command, such as random selection. However, the invention is not limited thereto.

In step S13, the address definition module 25 enables each of the signal transmitting and receiving elements 120 to correspond to one address parameter. In one embodiment, the result of corresponding each of the signal transmitting and receiving elements 120 to the address parameter may be recorded by the micro detection and treatment device 10 itself. Therefore, as long as the step S13 is executed once, it is not necessary to executed again, but is not limited to this.

In step S14, in one embodiment, the startup sequence setting module may set the startup sequence mode according to the control command transmitted by the user. In another embodiment, the startup sequence setting module 30 may set the startup sequence mode according to a predetermined command. As a result, the startup sequence setting module may generate a command to the startup module 35 for starting the signal transmitting and receiving elements 120 based on the startup sequence mode. However, the invention is not limited thereto.

In step S15, the startup module 35 transmits the actual startup signal to the corresponding signal transmitting and receiving element 120 according to the startup sequence mode selected in step S14, so that the signal transmitting and receiving element 120 corresponding to the specific address parameter transmits the first power. signal. However, the invention is not limited thereto.

In step S16, the startup module 35 transmits the actual startup signal to the corresponding signal transmitting and receiving elements 120 according to the startup sequence mode selected in step S14, so that the signal transmitting and receiving elements 120 receive the reflection signals, wherein the signal transmitting and receiving elements 120 in step S15 may be inconsistent with the signal transmitting and receiving elements 120 in step S16. In one embodiment, the execution period of the step S15 may partially overlap the execution period of the step S16. For example, when some of the signal transmitting and receiving elements 120 transmit the first power signal, the other signal transmitting and receiving elements 120 may receive the reflection signals. However, the invention is not limited thereto.

In step S17, the micro detection and treatment device 10 may transmit the received reflection signals to the cloud server 250 through the user operating device 150, and the cloud server 250 may integrate the reflection signals through a special algorithm to integrate the actual image. Since "how to integrate the image" is known to those skilled in the art and and is not the focus of the present invention, so that it will not be described in detail herein. In addition, in one embodiment, the cloud server 250 may include an automatic analysis algorithm to automatically analyze the position of the image to be treated from the image, and transmit the information back to the user operating device 15 or the micro detection and treatment device 10. In another embodiment, the cloud server 250 may integrate only the image without determining the position to be treated (the determination of the position to be treated can be made by a professional, such as a doctor). In one embodiment, when the image is integrated, either the cloud server 250 or the user operating device 15 may correspond the image to the address parameter of the signal transmitting and receiving element 120, and each address parameter is displayed on the image for allowing the user to be conveniently aware of the address parameter corresponding to each portion on the target object 500, so that the user may directly select the address parameter corresponding to the portion to be treated through the user operating device 15, as shown in FIG. 3(B). However, the invention is not limited thereto.

As long as it is reasonable and achievable, the aforementioned steps S11 to S17 can be arbitrarily increased, decreased, modified, or simultaneously executed. Therefore, the image-capturing procedure of the present invention can be completed. Accordingly, the user may obtain an image of the target object detected by the ultrasonic wave, and obtain information of the portion to be treated from the image.

Figure 5:
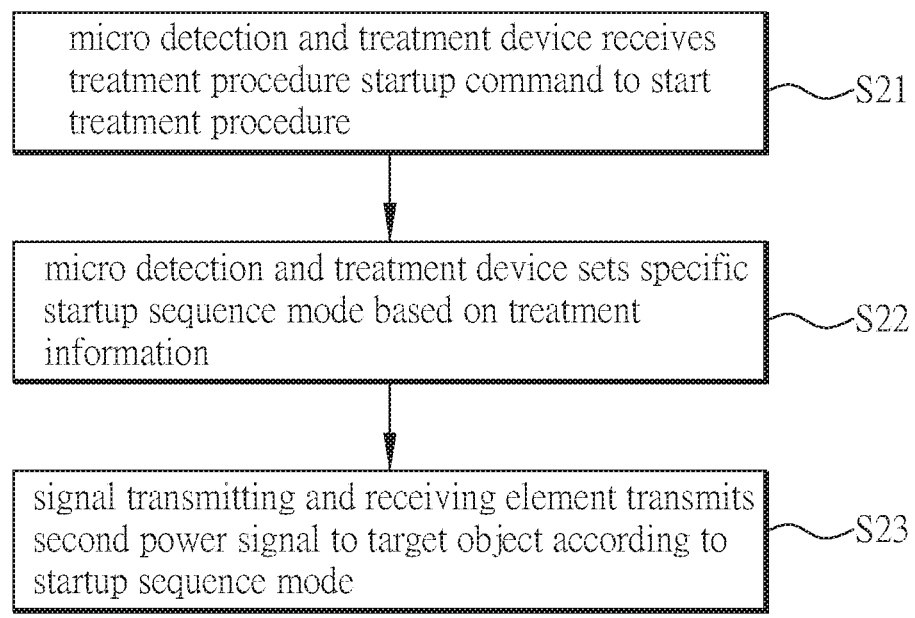
FIG. 5 is a flow chart illustrating the steps of a treatment procedure of the biological object image-capturing and treatment method according to an embodiment of the present invention.

FIG. 5 is a flow chart illustrating the steps of a treatment procedure of the biological object image-capturing and treatment method according to an embodiment of the present invention, which is performed by the biological object image-capturing and treatment system 1. First, step S21 is executed, in which the micro detection and treatment device 10 receives a treatment procedure startup command to start the treatment procedure. Then, step S22 is executed, in which the micro detection and treatment device 10 sets a specific startup sequence mode based on treatment information. Then, step S23 is executed, in which the signal transmitting and receiving element 120 corresponding to the specific address parameter sequentially or simultaneously transmits the second power signal to the target object 500 according to the startup sequence mode.

In step S21, in one embodiment, the user may use the user operating device 150 to transmit a control command to the micro detection and treatment device 10 for enabling the micro detection and treatment device 10 to enter the treatment procedure. For example, when being aware of the portion to be treated, the doctor may use the user operating device 150 to input the control command so as to control the micro detection and treatment device 10 to enter the treatment procedure. In another embodiment, when the cloud server 250 has the ability to automatically analyze the portion to be treated, the cloud server 250 may directly transmit data to the micro detection and treatment device 10, thereby allowing the micro detection and treatment device 10 to automatically enter the treatment procedure. However, the invention is not limited thereto.

In step S22, the treatment information may be defined as "information of the portion to be treated" or "information on which the signal transmitting and receiving element 120 needs to be started", and the startup sequence module 30 may set the startup sequence mode according to the treatment information. In one embodiment, the user causes the startup sequence module 30 to select a specific startup sequence mode by using a control command transmitted by the user operating device 150. In another embodiment, the micro detection and treatment device 10 or the cloud server may also automatically analyze an appropriate startup sequence mode according to the portion of the image that needs to be treated through a predetermined algorithm. In one embodiment, either the cloud server 250 or the user operating device 150 may correspond the image to the address parameters of the signal transmitting and receiving elements 120, and each address parameter may be displayed on the image to allow the user to be aware of the address parameter corresponding to each portion on the target object 500. Therefore, the user may directly select the address parameter corresponding to the portion to be treated through the user operating device 15, as shown in FIG. 3(B). However, the invention is not limited thereto.

In step S23, the startup module 35 transmits the actual startup signal to the corresponding signal transmitting and receiving elements 120 according to the startup sequence mode selected in step S14, so that the signal transmitting and receiving elements 120 actually transmit the ultrasonic signals for treatment (i.e., the second power signals). However, the invention is not limited thereto.

As long as it is reasonable and achievable, the aforementioned steps S21 to S23 can be arbitrarily increased, decreased, modified, or executed simultaneously. Therefore, the image-capturing procedure of the present invention can be completed. Accordingly, the user may obtain an image of the target object detected by the ultrasonic wave, and obtain information of the portion to be treated from the image.

Figure 6:
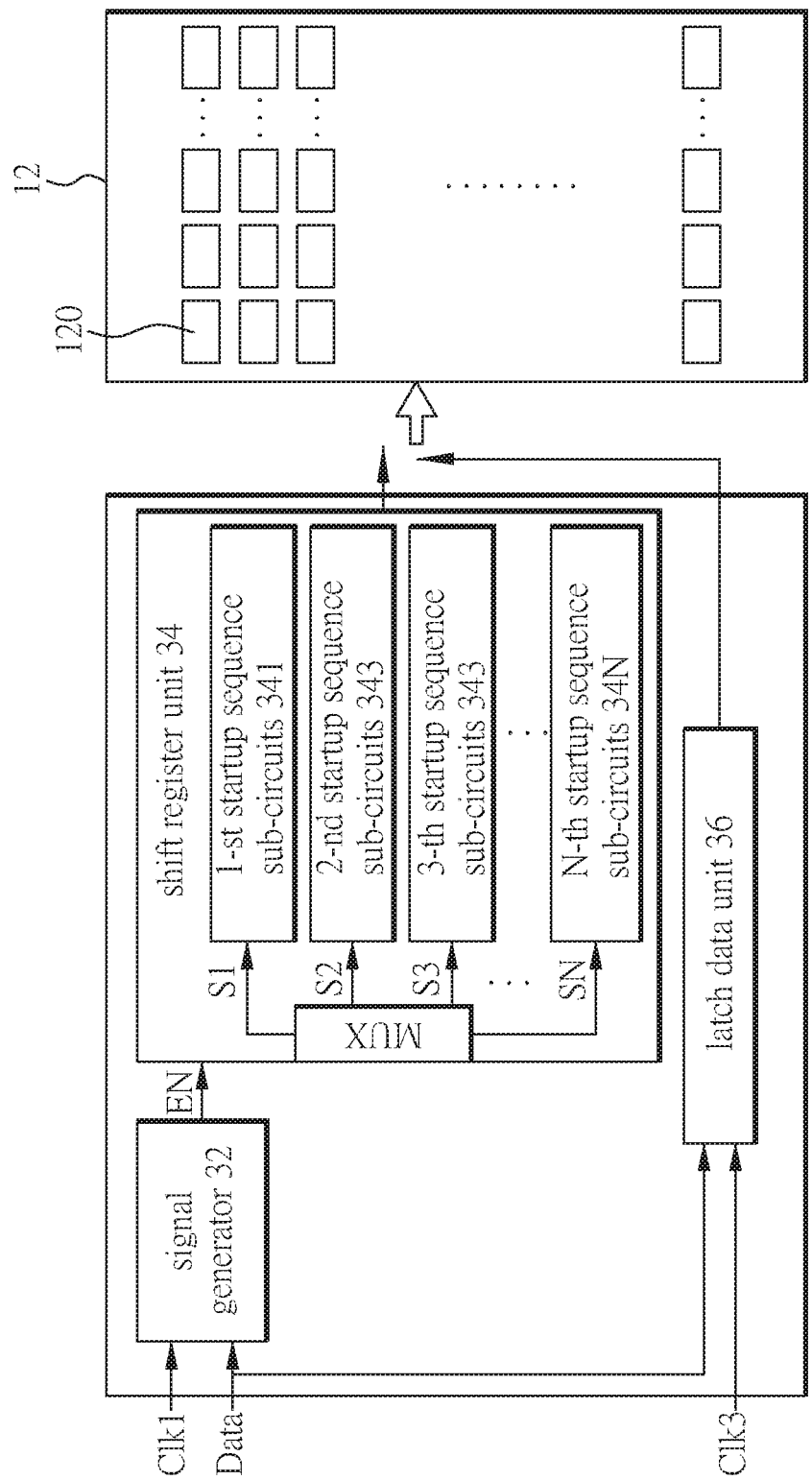
FIG. 6 is a circuit diagram of a startup sequence setting module and a startup module according to an embodiment of the invention.

The functions of the startup sequence setting module 30 and the startup module 35 of the present invention may be implemented by a digital logic circuit, which is described by way of an example in the following, but the invention is not limited to the example. FIG. 6 is a circuit diagram of the mode sequence setting module 30 and the startup module 35 according to an embodiment of the invention, and please refer to FIG. 1 to FIG. 5 at the same time.

As shown in FIG. 6, the detailed structure of the startup sequence setting module 30 and the startup module 35 may include a signal generator 32, a shift register unit 34, and a latch data unit 36. The shift register module 34 is coupled to the signal generator 32, and includes 1-st to N-th startup sequence sub-circuits 341-34N, wherein each of the startup sequence sub-circuits 341-34N corresponds to a startup sequence mode. The latch data unit 36 outputs a latch signal, and the latch signal is latched with the output of each of the startup sequence sub-circuits 341-34N.

In one embodiment, the signal generator 32 receives a first clock signal (Clk1) and a data signal (Data), and generates a second clock signal (hereinafter referred to as an enable signal (EN)) according to a first clock signal (Clk) and the data signal (Data). The shift register module 34 receives the enable signal, and multiplexes and shifts the data signal (Data) according to the enable signal (EN), thereby generating N address signals (S1~SN), wherein each of the address signals (S1~SN) controls the output signal (i.e., startup signal) of one of the startup sequence sub-circuits 341~34N, thereby controlling whether the startup sequence mode is ready to start. The latch data unit 36 performs an AND operation on the output signals (i.e., start signals) of the startup sequence sub-circuits 341~34N according to the data signal (Data) and a third clock signal (Clk3). As a result, one of the startup sequence modes is actually started, and thus the signal transmitting and receiving elements 120 transmit or receive signals according to the startup sequence mode.

In one embodiment, the first clock signal (clk1), the data signal (data), and the third clock signal (clk3) may be regarded as the control command transmitted by the user to the micro detection and treatment device 10 through the user operating device 150; for example, a doctor assigns and selects signal transmitting and receiving elements 120 of specific address parameters for the portion to be treated.

In one embodiment, the detailed structure may include at least one AND gate, wherein each AND gate is used to perform a logic operation on one of the address signals (S1~SN) and one of the startup signals (corresponding to one of the signal transmitting and receiving elements). In one embodiment, the quantity of the AND gates is equal to the product of the quantity of address signals (S1~SN) and the quantity of the startup signals.

As a result, the signal transmitting and receiving elements 120 may perform signal transmitting and receiving according to a specific startup sequence mode, so as to prevent the adjacent signal transmitting and receiving elements 120 from performing signal transmitting and receiving in the same period.

In one embodiment, each of the startup sequence sub-circuits 341~34N includes a plurality of flip-flops. In one embodiment, each startup sequence sub-circuit includes 32 flip-flops. In one embodiment, in order to achieve the i-th startup sequence mode (i.e., the signal transmitting and receiving elements 120 are started in a manner of spacing i signal transmitting and receiving elements 120), the key point is such that the output signal of the (i+1)-th flip of the i-th startup sequence sub-circuit 34i has to be coupled to the input end of the 1-st flip-flop, while the subsequent flip flops are applied in a similar manner, so as to achieve the i-th startup sequence mode, where i is a positive integer less than or equal to N. As a result, the startup sequence sub-circuits 341~34N may respectively implement the 1-st to N-th startup sequence modes.

With the biological object image-capturing and treatment system and method of the present invention, it is able to not only integrate the image-capturing function and the treatment function into the same micro detection and treatment device 10, but also greatly reduce the interference between adjacent signal channels through a startup sequence of special signal transmitting and receiving elements.

Although the present invention has been explained in relation to its preferred embodiment, it is to be understood that many other possible modifications and variations can be made without departing from the spirit and scope of the invention as hereinafter claimed.

What is claimed is:

1. A biological object image-capturing and treatment system for performing an image-capturing procedure and a treatment procedure, comprising:
 a micro detection and treatment device including a signal transmitting and receiving element array having a plurality of signal transmitting and receiving elements, wherein adjacent at least two elements of the plurality of the signal transmitting and receiving elements are configured to transmit signals or receive signals during different periods,
 wherein, when performing the image-capturing procedure, at least one element of the plurality of signal transmitting and receiving elements transmits a first power signal and, when performing the treatment procedure, at least one element of the plurality of signal transmitting and receiving elements transmits a second power signal, where the first power signal has a power different from that of the second power signal;
 wherein a diameter of each one of the plurality of the signal transmitting and receiving elements is equal to or smaller than 10000 micrometers (µm), and the micro detection and treatment device is for being inserted into a human body;
 wherein the treatment procedure comprises a first treatment mode and a second treatment mode, the first treatment mode is set to transmit the second power signal to different positions of a target object by using one element of the plurality of signal transmitting and receiving elements, the second treatment mode is set to transmit the second power signal to the different positions of the target object by using atleast a part of the plurality of signal transmitting and receiving elements;
 wherein the micro detection and treatment device further comprises a startup sequence setting module and a startup module, the startup sequence setting module controls the plurality of signal transmitting and receiving elements to perform a startup sequence mode of a plurality of startup sequence modes for shifting transmitting timing and receiving timing of the adjacent at least two elements of the plurality of signal transmitting and receiving elements, and the startup module generates a plurality of startup signals according to the startup sequence mode;
 wherein, a detailed structure of the startup sequence setting module and the startup module comprises a signal generator, a shift register unit, and a latch data unit, wherein the shift register unit is coupled to the signal generator and comprises a plurality of startup sequence sub-circuits, wherein each of the startup sequence sub-circuits corresponds to a startup sequence mode of the plurality of startup sequence modes, and the latch data unit outputs a latch signal for performing an AND operation on the output of each of the startup sequence sub-circuits;
 wherein the biological object image-capturing and treatment system further comprises a user operating device, wherein the user operating device is integrated with a handle to form a handheld user operating device, the handle is provided with a button area, and the button area includes a plurality of buttons corresponding to the signal transmitting and receiving elements, wherein the handheld user operating device is combined with the biological object image-capturing and treatment system in a manner that the handheld user operating device is combined with a subsystem responsible for image-capturing procedure of the biological object image-capturing and treatment system, the handheld user operating device is combined with a subsystem responsible for treatment procedure of the biological object image-capturing and treatment system, the handheld user operating device is combined with a subsystem responsible for image-capturing procedure and a subsystem responsible for treatment procedure of the biological object image-capturing and treatment system while the subsystems are not a common system, the handheld user operating device is combined with a conventional treatment system and a subsystem responsible for image-capturing procedure of the biological object image-capturing and treatment system while the conventional treatment system and the subsystem are not a common system, or the handheld user operating device is combined with a conventional treatment system and a subsystem responsible for image-capturing procedure of the biological object image-capturing and treatment system while the conventional treatment system and the subsystem are a common system.

2. The biological object image-capturing and treatment system of claim 1, wherein, when the image-capturing procedure is performed, a single signal transmitting and receiving element or at least two elements of the plurality of signal transmitting and receiving elements transmits the first power signal to different positions of the target object, and a single signal transmitting and receiving element or at least two elements of the plurality of signal transmitting and receiving elements receives reflection signals reflected from different positions of the target object at different time points.

3. The biological object image-capturing and treatment system of claim 2, further comprising a cloud server, which obtains the reflection signals and integrates the reflection signals into an image.

4. The biological object image-capturing and treatment system of claim 1, wherein the micro detection and treatment device is a disposable device.

5. The biological object image-capturing and treatment system of claim 1, wherein the power of the first power signal is less than that of the second power signal, or a frequency of the first power signal is less than that of the second power signal.

6. The biological object image-capturing and treatment system of claim 1, wherein each of the signal transmitting and receiving elements corresponds to an address parameter, the address parameters correspond to a lookup table, a user operating device displays the address parameters by the lookup table, and the address parameters are presented in a form of selectable buttons.

7. The biological object image-capturing and treatment system of claim 1, wherein the micro detection and treatment device further comprises a high voltage control module for detecting whether the adjacent at least two elements of the plurality of signal transmitting and receiving elements have received a startup signal of the plurality of startup signals, and if yes, the high voltage control module controls the adjacent at least two elements of the plurality of signal transmitting and receiving elements not to transmit signals.

8. The biological object image-capturing and treatment system of claim 1, wherein the micro detection and treatment device further comprises a delay module for enabling signal transmitting periods of the adjacent at least two elements of the plurality of signal transmitting and receiving elements to have a time interval.

9. A biological object image-capturing and treatment method performed by a biological object image-capturing and treatment system comprising a micro detection and treatment device including a plurality of signal transmitting and receiving elements arranged in an array, wherein adjacent at least two elements of the plurality of the signal transmitting and receiving elements are configured to transmit signals or receive signals during different periods, the method comprising the steps of:
when performing an image-capturing procedure, transmitting a first power signal by at least one element of the plurality of signal transmitting and receiving elements;
when performing a treatment procedure, transmitting a second power signal by at least one element of the plurality of signal transmitting and receiving elements, wherein the first power signal has a power or a frequency different from that of the second power signal; and
when the image-capturing procedure and the treatment procedure are not performed, the plurality of signal transmitting and receiving elements are standby;
wherein a diameter of each one of the plurality of the signal transmitting and receiving elements is equal to or smaller than 10000 micrometers (m), and the micro detection and treatment device is for being inserted into a human body;
wherein the treatment procedure comprises a first treatment mode and a second treatment mode, the first treatment mode is set to transmit the second power signal to different positions of a target object by using one element of the plurality of signal transmitting and receiving elements, the second treatment mode is set to transmit the second power signal to the different positions of the target object by using at a part of the plurality of signal transmitting and receiving elements;
wherein the micro detection and treatment device further comprises a startup sequence setting module and a startup module, the startup sequence setting module controls the plurality of signal transmitting and receiving elements to perform a startup sequence mode of a plurality of startup sequence modes for shifting transmitting timing and receiving timing of the adjacent at least two elements of the plurality of signal transmitting and receiving elements, and the startup module generates a plurality of startup signals according to the startup sequence mode;
wherein, a detailed structure of the startup sequence setting module and the startup module comprises a signal generator, a shift register unit, and a latch data unit, wherein the shift register unit is coupled to the signal generator and comprises a plurality of startup sequence sub-circuits, wherein each of the startup sequence sub-circuits corresponds to a startup sequence mode of the plurality of startup sequence modes, and the latch data unit outputs a latch signal for performing an AND operation on the output of each of the startup sequence sub-circuits;
wherein the biological object image-capturing and treatment system further comprises a user operating device, wherein the user operating device is integrated with a handle to form a handheld user operating device, the handle is provided with a button area, and the button area includes a plurality of buttons corresponding to the signal transmitting and receiving elements, wherein the handheld user operating device is combined with the biological object image-capturing and treatment system in a manner that the handheld user operating device is combined with a subsystem responsible for image-capturing procedure of the biological object image-capturing and treatment system, the handheld user operating device is combined with a subsystem responsible for treatment procedure of the biological object image-capturing and treatment system, the handheld user operating device is combined with a subsystem responsible for image-capturing procedure and a subsystem responsible for treatment procedure of the biological object image-capturing and treatment system while the subsystems are not a common system, the handheld user operating device is combined with a conventional treatment system and a subsystem responsible for image-capturing procedure of the biological object image-capturing and treatment system while the conventional treatment system and the subsystem are not a common system, or the handheld user operating device is combined with a conventional treatment system and a subsystem responsible for image-capturing procedure of the biological object image-capturing and treatment system while the conventional treatment system and the subsystem are a common system.

10. The biological object image-capturing and treatment method of claim 9, further comprising a step of: when the image-capturing procedure is performed, using a single signal transmitting and receiving element or at least two elements of the plurality of signal transmitting and receiving elements to transmit the first power signal to different positions of the target object, and using a single signal transmitting and receiving element or at least two elements of the plurality of signal transmitting and receiving elements to receive reflection signals reflected from different positions of the target object at different time points.

11. The biological object image-capturing and treatment method of claim 10, further comprising a step of: using a cloud server to obtain the reflection signals and using the cloud server to integrate the reflection signals into an image.

12. The biological object image-capturing and treatment method of claim 9, wherein the micro detection and treatment device is a disposable device.

13. The biological object image-capturing and treatment method of claim 9, wherein the power of the first power signal is less than that of the second power signal, or the frequency of the first power signal is less than that of the second power signal.

14. The biological object image-capturing and treatment method of claim 9, wherein each of the signal transmitting and receiving elements corresponds to an address parameter, the address parameters correspond to a lookup table, a user operating device displays the address parameters by the lookup table, and the address parameters are presented in a form of selectable buttons.

15. The biological object image-capturing and treatment method of claim 9, further comprising a step of: using a high voltage control module included in the micro detection and treatment device to detect whether the adjacent at least two elements of the plurality of signal transmitting and receiving elements have received a startup signal of the plurality of startup signals, and if yes, using the high voltage control module to control the adjacent at least two elements of the plurality of signal transmitting and receiving elements not to transmit signals, and if no, the high voltage control module outputs an enable signal for the adjacent at least two elements of the plurality of signal transmitting and receiving elements.

16. The biological object image-capturing and treatment method of claim 9, further comprising a step of: using a delay module included in the micro detection and treatment device to enable signal transmitting periods of the adjacent at least two elements of the plurality of signal transmitting and receiving elements to have a time interval.

* * * * *